(12) United States Patent
Citernesi

(10) Patent No.: US 6,953,571 B2
(45) Date of Patent: Oct. 11, 2005

(54) COSMETIC OR PHARMACEUTICAL COMPOSITION FOR TOPICAL USE TO PREVENT OR DIFFER ANDROGENETIC ALOPECIA

(75) Inventor: Ugo Raffaello Citernesi, Usmate Velate (IT)

(73) Assignee: Farmaka s.r.l., Crandate (IT)

( * ) Notice: Subject to any disclaimer, the term of this patent is extended or adjusted under 35 U.S.C. 154(b) by 0 days.

(21) Appl. No.: 10/789,082

(22) Filed: Feb. 27, 2004

(65) Prior Publication Data

US 2004/0197887 A1 Oct. 7, 2004

(30) Foreign Application Priority Data

Feb. 28, 2003 (IT) .................................... MI2003A0369

(51) Int. Cl.[7] ................................................ A61K 7/06
(52) U.S. Cl. .................... 424/70.1; 424/94.1; 424/94.2; 424/94.4; 424/780; 514/880
(58) Field of Search ..................... 514/880; 424/94.4, 424/94.2, 94.1, 780, 70.1; 132/202

(56) References Cited

U.S. PATENT DOCUMENTS

| | | | | |
|---|---|---|---|---|
| 4,684,635 A | * | 8/1987 | Orentreich et al. | ......... 514/170 |
| 5,422,371 A | * | 6/1995 | Liao et al. | .................... 514/560 |
| 5,514,672 A | * | 5/1996 | Bazzano | ...................... 514/168 |
| 5,756,092 A | | 5/1998 | Michelet et al. | |
| 6,110,906 A | * | 8/2000 | Labrie et al. | ................ 514/163 |
| 6,733,776 B1 | * | 5/2004 | Li et al. | ...................... 424/450 |

FOREIGN PATENT DOCUMENTS

| | | | | |
|---|---|---|---|---|
| JP | 62012721 | | 1/1987 | |
| WO | WO 01/66702 A1 | * | 9/2001 | ............ C12N/9/02 |

OTHER PUBLICATIONS

Chen et al, J Invest Dermatol, 2002, vol. 119, p. 992–1007.*

English Abstract corresponding to Ref. A3, Morita Yasahiro, Patent No. JP62012721, Published Jan. 21, 1987.

* cited by examiner

*Primary Examiner*—Leon B. Lankford, Jr.
*Assistant Examiner*—Allison M. Ford
(74) *Attorney, Agent, or Firm*—Lucas & Mercanti, LLP

(57) ABSTRACT

A cosmetic-pharmaceutical composition for topical use against human alopecia containing a pool of enzymes of the specific hydroxisteroido-dehydrogenase group in the presence of nicotinamido-adenine-dinucleotide coenzyme and a vasodilator, the whole being complexed with phospholipids in solution.

6 Claims, 3 Drawing Sheets

PRODUCED FORMAZAN IN HAIR BULB CULTURES AFTER 5 AND 10 INCUBATION DAYS

COSMETIC OR PHARMACEUTICAL COMPOSITION FOR TOPICAL USE TO PREVENT OR DIFFER ANDROGENETIC ALOPECIA

This patent application claims the benefit of priority from Italian Patent Application No. MI2003A000369 filed Feb. 28, 2003, the contents of which are incorporated herein by reference.

BACKGROUND OF INVENTION

1. Field of Invention

The present invention relates to a composition usable in the preventive and/or curative cosmetic-therapeutic treatment of alopecia or generally of anomalous hair defluvium.

In particular the present invention relates to an enzymatic composition which prevents or blocks the causes of hair loss.

2. Prior Art

As it is known, hair loss is due to various causes, among which the most reliable is attributable to the action of particular enzymes which reduce the level of sex hormones by aiding their transformation. So, for example, in man, testosterone may be easily converted, under certain conditions, into dihydrotestosterone which is mainly responsible for atrophy and death of hair bulbs. This reduction reaction in fact can be catalyzed by 5-alpha-reductase being present in the male gonads and prostate.

On the other hand, the general capability of certain enzymes to act in an oxidative or reductive sense, according to the functional conditions, has induced scientists to seek out combinations of enzymes and other kinds of substances for orienting the reaction in the desired direction. See, for example, U.S. Pat. No. 5,756,092, JP 62 012 721 and WO 01/66702 in this regard.

In particular, the last named document, i.e. international patent application WO 01/66702 A1, relates to the use of 3-α-hydroxysteroido-oxido-reductase (3-α-HSOR) and a coenzyme with the intention of oxidizing dihydrotestosterone (DHT), thus converting it into a form that may be possibly neutral with respect to hair bulbs.

The tests carried out by the applicant of the present application, with the same intention as the above named application, have shown however that the proposed combining of 3-α-oxidoreductases with NADP(H)/NAD(H) is not sufficient to achieve the desired effect.

SUMMARY OF THE INVENTION

The applicant has completed studies and has found that a combination of 3-β-hydroxysteroido-dehydrogenase (3-β-HSD) and/or 17-α-hydroxysteroido-dehydrogenase (17-α-HSD), having a molecular weight of about 100.000 D, with nicotinamido-adenin-dinucleotide (NAD) in the presence of phospholipids achieves a desired effect concerning preventing alopecia.

An object of the present invention is therefore to provide a composition of hydroxysteroido-dehydrogenase (HSD), nicotinamido-adenine-dinucleotide (NAD) and phospholipids in a suitable water medium for direct application on the scalp. Since in the presence, for instance, of 3-β- and 17-β-HSD as well as of NAD, testosterone changes to 4-androsterone-3,17-dione, that is present in the organism as an excretion product (urine) only. It was tried with HSDs whose oxidizing action is similar to that of said substances, and perform not only in vitro but in vivo (skin) too, without unbalancing the internal hormone equilibrium, and that will be obtainable in a relatively simple manner.

Knowing further that a single enzyme is generally not enough to catalyze certain biochemical transformations, an enzymatic pool was characterized and tested substantially comprising 3-β-hydroxysteroido-oxido-reductase (3-β-HSOR) and 17-α-hydroxysteroida-oxido-reductase (17-α-HSOR), having a molecular weight of about 100,000 Daltons and being extractable from microorganism cultures such as *Pseudomonas testosteroni*.

This enzyme, or rather enzymatic pool, was thus found in 3-β-hydroxysteroido-oxido-reductase (3-β-HSOR) and 17-α-hydroxysteroido-oxido-reductase (17-α-HSOR), having a molecular weight equal to 100,000 Daltons and being extractable from microorganism cultures such as *Pseudomonas testosteroni*.

BRIEF DESCRIPTION OF THE DRAWINGS

The invention, together with further objects and advantages thereof, may best be understood by reference to the following descriptions taken in conjunction with the accompanying drawings wherein.

DETAILED DESCRIPTION OF THE INVENTION

Figure 1:
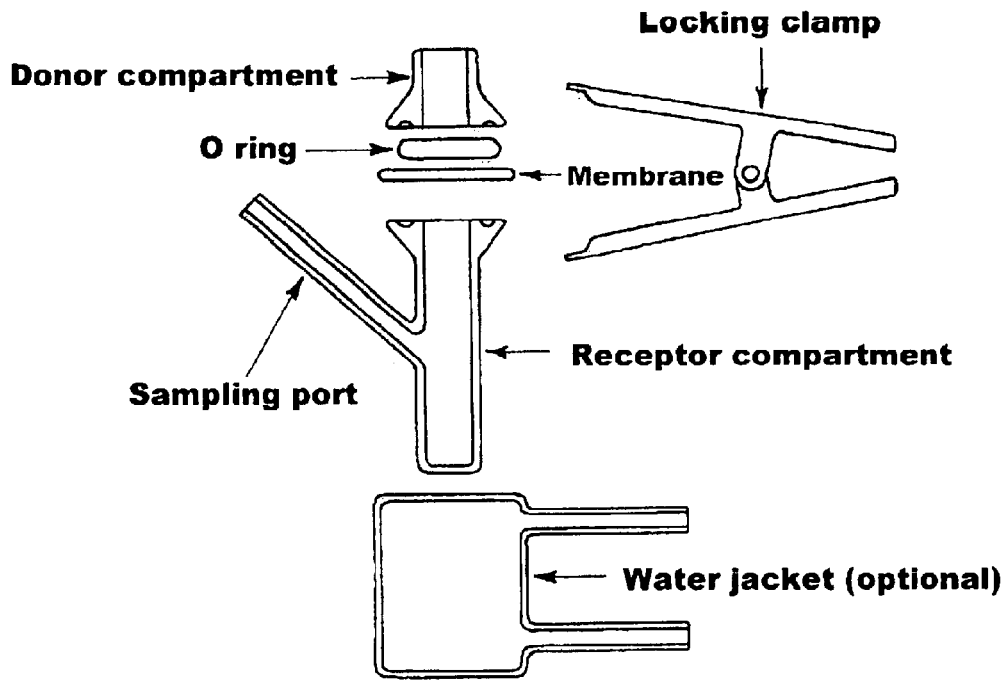
FIG. 1 schematically shows a longitudinal section of the cell type as used with relevant fittings.
Figure 1:
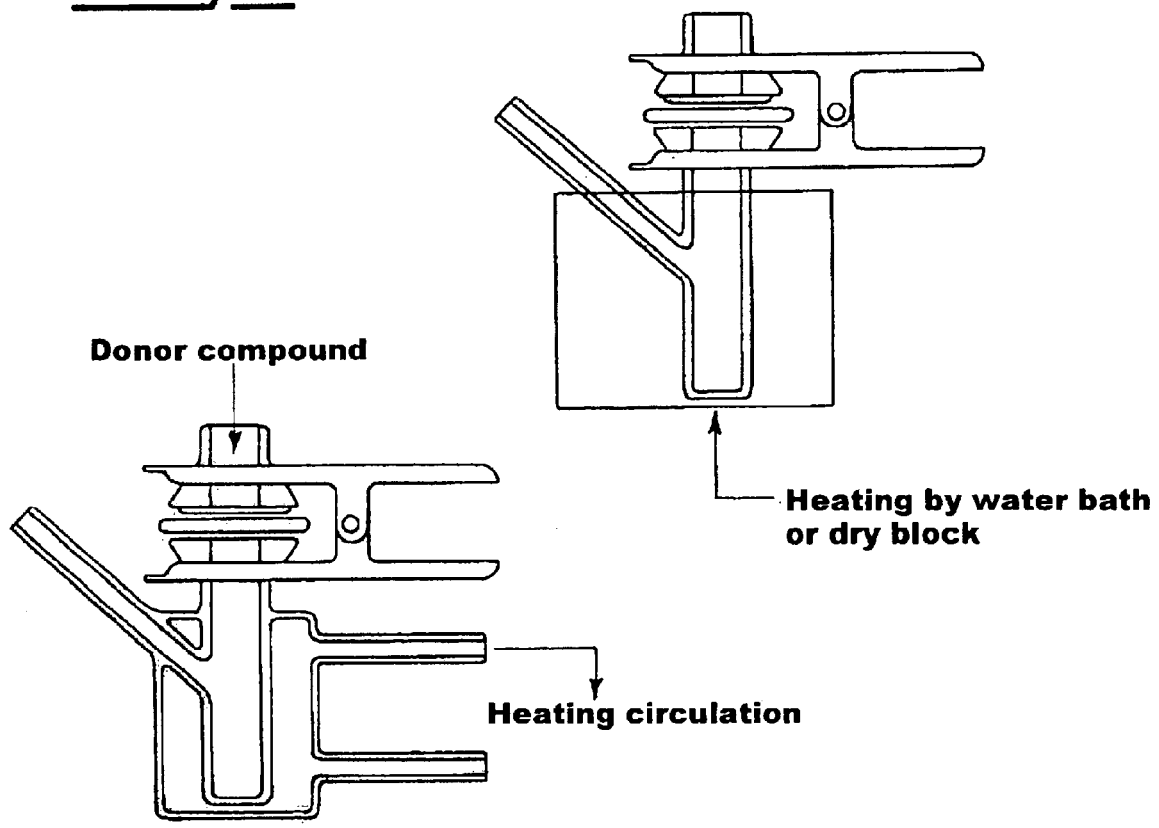

In one aspect of the invention, there is provided a composition usable in the preventive and/or curative cosmetic-therapeutic treatment of alopecia or generally of anomalous hair defluvium. More specifically, the present invention relates to an enzymatic composition which prevents or blocks the causes of hair loss. The composition is thus designed for topical use in the cosmetic or pharmaceutical field and is characterized in that it comprises an enzymatic pool, a coenzyme and a vasodilator; complexed with phospholipids in solution.

In preferred aspects of the invention, the enzymatic pool comprises 3-β-hydroxysteroido-oxido-reductase (3-β-HSOR) and 17-α-hydroxysteroido-oxido-reductase (17-α-HSOR), both having a MW of about 100,000 Daltons; the coenzyme is nicotinamido-adenin-dinucleotide (NAD); and the vasodilator is a nicotinic acid derivative such as thurfyl nicotinate or other such derivatives known to those of ordinary skill in the art. The compositions of the present invention can also further comprise auxiliaries, additives, drugs and active principles which enhance or aid the therapeutic and/or cosmetic effectiveness of the inventive compositions.

In another aspect of the invention, there is provided a method of treating alopecia in mammals. The method includes topically applying an effective amount of a composition described herein on the affected area of a mammal in the need of such treatment. In most cases, of course, the mammal is a human male and the affected area is the scalp. It is contemplated, however, that the compositions are useful in treating alopecia in other mammals.

In a still further aspect of the invention, there is provided a method of treating light defects in the skin and appendages in mammals. This aspect includes applying an effective amount of a composition described herein topically to the affected area of a mammal in the need of such treatment.

The amount of the composition applied to the affected areas of the scalp or skin is an amount which is effective to produce the desired results. It is contemplated that the compositions will be applied one or more times daily to the areas requiring treatment. Exact treatment regimens will depend upon the mammal and condition being treated. Selection of the effective amount and duration of treatment will be apparent to those of ordinary skill and can be determined without undue experimentation.

*Pseudomonas testosteroni* was cultured in a minimum medium containing 0.2% of dihydrotestosterone (DHT) as the sole source of energy and, after suitable selection and purification through subsequent liquid cultures in a microhalophile milieu and incubation at 37° C., it was treated by sonication in order to lyse the cell walls and obtain the culture broth. The latter was then subjected to ultrafiltration by setting the cut-off of the resulting enzymatic pool at 150,000 and 100,000 with a view to shut out the 3-α-hydroxysteroido-dehydrogenases which have a molecular weight of about 47,000, and to isolate instead 3-β- and 17-α-hydroxysteroido-dehydrogenases with molecular weight of about 100,000 D. The ultrafiltrate liquid was then concentrated and lyophilized, to obtain a hygroscopic powder wherein said selected enzymes have a concentration of not less than 75%.

To the thus obtained powder with enzymatic activity NAD (nicotinamido-adenine-dinucleotide) was then added and the whole was dissolved in water and alcohol at 20%, to which an amount of phospholipids of vegetable origin was added, sufficient to form a semisolid mixture that was then thoroughly kneaded in a magnetic mixer for 12 hours. Water was then added to the semisolid mixture in order to obtain the development of liposomes, and after centrifugation at 5000 rpm for 30 minutes, the aqueous suspension was concentrated under vacuum to have a total removal of solvents and formation of a powder that will be rehydrated to give liposome and phospholipid complexes. It is essential to point out in this regard that the coenzyme used was nicotinamido-adenine-dinucleotide not hydrogenated (namely NAD and not NAD(H)).

The active solution of 3-β- and 17-α-HSOR, NAD and phospholipids was tested in vitro to verify and determine the absorption through semi-permeable membranes of artificial or natural origin. To this end, thermostated glass cells of Franz type were used by following a standard protocol according to the UNIPRO suggestions (Cosmesi Dermatologica, year 12, No. 61, April–June 1997, page. 31–40) with slights changes.

FIG. 1 shows schematically in longitudinal section the cell type as used with relevant fittings.

Fresh pig skin was utilized after having been reduced to 1 mm thick by dermabrasion by accurate removal of fatty parts and by keeping unaltered the horny layer, epidermis and a portion of true skin. By means of a dinking machine circular membranes were obtained with a diameter of 20 mm, which were then examined through an electron microscope to verify the absence of unevenness or injuries, and placed immediately next in Franz type cells with the true skin towards the receptor liquid (downwards) and the horny layer towards the donor liquid (upwards). The duration of each test was 24 hours. Each used a substantially cylindrical glass cell having a radius of 20 mm with an exchange circular surface of 12.56 cm$^2$ and contained a receptor liquid volume of 22 ml. The test receptor liquid was formed by sterile distilled water having the following saline composition: NaCl 0.14 M+K$_2$HPO$_4$2 mM+KH$_2$PO$_4$0.4 mM, with the addition of 100 IU of penicillin and 100 mg of streptomycin per ml. The thermoregulation was obtained by means of a continuous circulation of the liquid through a thermostat/cryostat system of LKB at 33°±1° C. At regular time intervals of 15 minutes, there was effected by a syringe a taking of 10 μl (10 mg) of receptor liquid, so as to calculate the amount of examined complex passed through the pig membrane into the receptor liquid in a time unit.

The enzymatic complex dissolved in water and tested had the following composition: 0.5% of 3-β-HSOR+17-α-HSOR; 0.5% of NAD and 99% of phospholipids. For comparison purposes in a parallel test, the phospholipids were substituted by an equal amount (99%) of an inert vehicle formed by maltodextrins. In order to act under the same osmotic pressure conditions, both the test sample and the reference sample were dissolved in equal amounts of receptor liquid up to an arbitrarily selected and fixed concentration of 10%. Since the amount of each sample placed on the membrane was in all tests of 2 g, it appears that the amount of tested enzyme was finally of 0.5 g×0.1 (=10%)×2 g=0.1 g. Such an amount was determined through an experimental route with preliminary tests aiming at assuming by subsequent steps the quantity of product regarded as necessary for an absorption evaluation such that it may be analytically determined.

The pads of defatted skin that were obtained as described above by means of a dinking machine were placed in the Franz type glass cells with the true skin contacting the receptor liquid, and the samples to be tested were applied on horny layer. At regular time intervals of 15 minutes starting from zero time, takings of 10 microliters of receptor liquid were then effected to calculate the amount of product passed through the skin membrane, from donor liquid to receptor liquid.

There are given in this connection, in table form, the results expressed as nitrogen percent found in receptor liquid, and originating from solutions of complexes of 3-β-HSOR+17-α-HSOR as enzymes and NAD) as a coenzyme, in the presence (With PL) and in absence of phospholipids (Without PL).

TABLE 1

| Time (minutes) | With PL | Without PL |
| --- | --- | --- |
| 1 | 0 | 0 |
| 2 | 0 | 0 |
| 3 | $1.81818 \times 10^{-7}$ | 0 |
| 4 | $2.13904 \times 10^{-7}$ | 0 |
| 5 | $1.81818 \times 10^{-6}$ | $2.12157 \times 10^{-7}$ |
| 6 | $9.56938 \times 10^{-6}$ | $2.17226 \times 10^{-7}$ |
| 7 | $1.15808 \times 10^{-5}$ | $1.21212 \times 10^{-6}$ |
| 8 | $1.39860 \times 10^{-5}$ | $1.62338 \times 10^{-6}$ |
| 9 | $1.81818 \times 10^{-5}$ | $1.95503 \times 10^{-6}$ |
| 10 | $1.67441 \times 10^{-5}$ | $2.11416 \times 10^{-6}$ |
| 11 | $2.02020 \times 10^{-5}$ | $3.63636 \times 10^{-6}$ |
| 12 | $2.13904 \times 10^{-5}$ | $5.07872 \times 10^{-6}$ |
| 13 | $2.42424 \times 10^{-5}$ | $7.27273 \times 10^{-6}$ |
| 14 | $2.59740 \times 10^{-5}$ | $9.09091 \times 10^{-6}$ |
| 15 | $2.79720 \times 10^{-5}$ | $1.25392 \times 10^{-5}$ |
| 16 | $3.63636 \times 10^{-5}$ | $1.95503 \times 10^{-5}$ |

Figure 2:
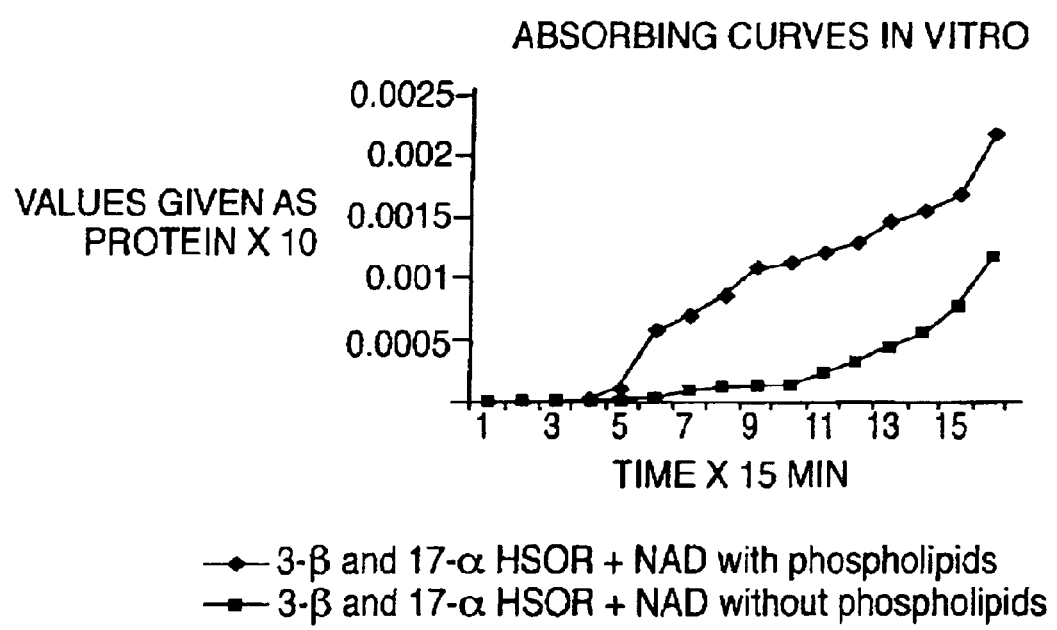
FIG. 2 schematically shows the results of table 1.

The results of table 1 are graphically schematized in FIG. 2. FIG. 2 represents the nitrogen percentage as a factor of Protein Content, which according to the Kieldahl method, (a worldwide standard for calculating protein content) corresponds to the formula nitrogen percentage×6.25=protein content, where 6.25 is the average protein factor.

In order to determine the presence and level of dehydrogenase activity in the used enzyme complex, the formazan method was adopted, according to which a colorless compound (a tetrazolium salt) changes to a colored compound (formazan) only in the presence of dehydrogenating oxidative reactions. Now, the dehydrogenases, such as HSROs, are enzymes that catalyze these reactions in various substrates, among which in mitochondria too, so that the conversion of tetrazolium into formazan can aid in evaluating the production of energy and activation of cell metabolisms by living cells. The conversion reaction can be stoichiometrically measured by dosing through spectroscopic route the formed formazan. By taking advantage of this principle, the cells can be incubated with different substances with a view to determinate the activity thereof and/or evaluate the toxicity level of the used substances. In our case, as a matter of fact, the possibly insufficient or dangerous effect of a substance would inhibit the activity of mitochondrial dehydrogenases and prevent therefore the conversion of tetrazolium into formazan. By dosing formazan with a spectrophotometer it is possible in contrast to establish the cell vitality level before and after treatment with the selected dehydrogenases.

Figure 3:
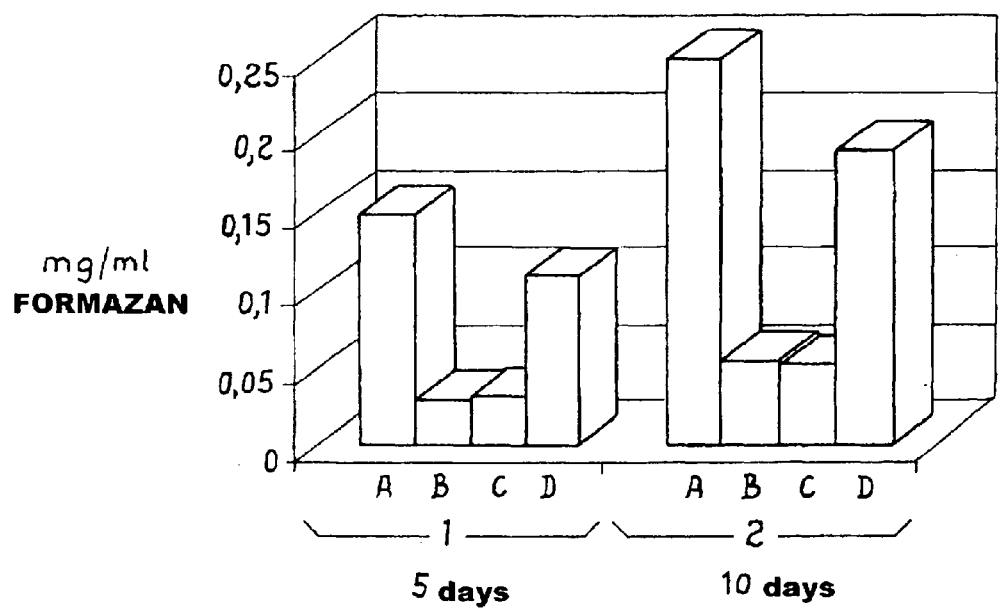
FIG. 3 shows results obtained when utilizing the forzman method.

The methodology used in the case of the present invention has foreseen: A) a base control carried out on hair bulbs only in Williams culture medium; B) an action on bulbs in Williams medium added with 10 ng/ml of DHT; C) as in B) but with the addition of 10 ng/ml of 3-β-HSOR+17-α-HSOR and further 10 ng/ml of hydrogenated NAD (NADH); and D) as in C) but by substituting NADH with an equivalent amount of NAD (not hydrogenated). The obtained results are schematically given in the form of a three-dimensional histogram in FIG. 3.

EXAMPLES

Examples of preparations usable for topical application according to the present invention are given below, wherein the values are percents by weight. The examples thus serve to provide further appreciation of the invention but are not meant in any way to restrict the effective scope of the invention.

Example 1

| Phospholipidic complex of enzyme 3-β-17-α-HSOR and NAD | |
|---|---|
| Ethyl alcohol at 70° | 75 |
| Soy phospholipids | 24 |
| HSOR | 0.5 |
| NAD | 0.25 |
| Base solution | |
| Capsicin 1:200 in alcohol 96 D | 0.5 |
| Methyl nicotinate | 0.2 |
| Ethyl alcohol 96 D | 20 |
| Carbitol | 7 |
| PEG-7/glyceryl cocoate DAB CG | 2.5 |
| Deionized water | 54.75 |
| Propylene glycol | 14 |
| Flavorings | 1 |
| Methionine + Cysteine HCl + Ornithine HCl + Biotin + Chondroitin sulfate | ana 0.01 |

Example 2

| The complex comprises the same components of Example 1 with the following percentages: | |
|---|---|
| Ethyl alcohol/Glycerin 40/60 | 75 |
| Soy phospholipids | 24 |
| HSOR | 0.5 |
| NAD | 0.25 |
| Thurfyl nicotinate | 0.25 |
| Base solution | |
| PEG 7/Glyceryl cocoate | 2.6 |
| Carbitol | 7 |
| Hyaluronic acid | 1 |
| Pentylene glycol | 3.5 |
| Rosemary extract | 0.5 |
| Green tea extract | 0.5 |
| Water | balance to 100 |

Example 3

| The complex has the same composition and percentages of Example 2. | |
|---|---|
| Base solution | |
| PEG 7/Glyceryl cocoate | 2.6 |
| Carbitol | 7 |
| Hyaluronic acid | 1 |
| Pentylene glycol | 3.5 |
| Copper chloride | 0.02 |
| Potassium iodide | 0.1 |
| Zinc chloride | 0.05 |
| Biotin + Methionine + Cysteine HCl + Ornithine HCl | ana 0.01 |
| Water | balance to 100 |

I claim:

1. A composition for topical use in the cosmetic or pharmaceutical field, comprising:
   a. an enzymatic pool which comprises 3-β-hydroxysteroid--oxidoreductase (3-β-HSOR) and 17-α-hydroxysteroid-oxidoreductase (17-α-HSOR), both having a MW of about 100,000 Daltons;
   b. a coenzyme which comprises nicotinamido-adenine-dinucleotide (NAD); and
   c. a vasodilator which comprises a nicotinic acid derivative;
complexed with phospholipids in solution.

2. The composition according to claim 1, wherein the nicotinic acid derivative is thurfyl nicotinate.

3. A method of treating alopecia in mammals, comprising:
   applying an effective amount of the composition of claim 1 topically to the affected area of a mammal in the need of such treatment.

4. The method of claim 3, wherein the mammal is a human.

5. The method of claim 4, wherein the human is male.

6. The method of claim 4, wherein said composition of claim 1 is applied to the scalp of the human.

* * * * *